United States Patent
Fowler et al.

(10) Patent No.: US 10,806,744 B2
(45) Date of Patent: Oct. 20, 2020

(54) EDIBLE COMPOSITION

(71) Applicant: Conopco, Inc., Englewood Cliffs, NJ (US)

(72) Inventors: Mark Ian Fowler, Huntingdon (GB); Huijun Wang, Shanghai (CN)

(73) Assignee: Conopco, Inc., Englewood Cliffs, NJ (US)

(*) Notice: Subject to any disclaimer, the term of this patent is extended or adjusted under 35 U.S.C. 154(b) by 0 days.

(21) Appl. No.: 15/755,510

(22) PCT Filed: Aug. 25, 2016

(86) PCT No.: PCT/EP2016/070118
§ 371 (c)(1),
(2) Date: Feb. 26, 2018

(87) PCT Pub. No.: WO2017/036926
PCT Pub. Date: Mar. 9, 2017

(65) Prior Publication Data
US 2018/0256620 A1 Sep. 13, 2018

(30) Foreign Application Priority Data
Sep. 3, 2015 (EP) .................... 15183639

(51) Int. Cl.
| A61K 31/7048 | (2006.01) |
| A23L 33/105 | (2016.01) |
| A61K 9/00 | (2006.01) |
| A61K 31/352 | (2006.01) |
| A61K 31/357 | (2006.01) |

(52) U.S. Cl.
CPC ........ *A61K 31/7048* (2013.01); *A23L 33/105* (2016.08); *A61K 9/0053* (2013.01); *A61K 31/352* (2013.01); *A61K 31/357* (2013.01); *A23V 2002/00* (2013.01)

(58) Field of Classification Search
CPC .............. A61K 31/7048; A61K 31/352; A61K 9/0053; A61K 31/357; A23L 33/105; A23V 2002/00
USPC ......................................................... 514/27
See application file for complete search history.

(56) References Cited

U.S. PATENT DOCUMENTS

| 2007/0248693 A1 | 10/2007 | Mazzio et al. |
| 2011/0027305 A1 | 2/2011 | Lee |

FOREIGN PATENT DOCUMENTS

| CN | 101259258 | 9/2008 |
| CN | 102319236 | 1/2012 |
| CN | 102949648 | 3/2013 |
| CN | 103566177 | 2/2014 |
| CN | 103933346 | 7/2014 |
| GB | 2226494 | 7/1990 |
| KR | 2011041808 | 4/2011 |
| WO | WO9852587 | 11/1998 |
| WO | WO2010135589 | 11/2010 |
| WO | WO2011045823 | 4/2011 |
| WO | WO2012168108 | 12/2012 |
| WO | WO2014086632 | 6/2014 |

OTHER PUBLICATIONS

Zhang et al. (J. Nat. Prod. 2010, 73, 548-552).*
Bidasee et al. (The Journal of Pharmacology and Experimental Therapeutics, (2000), vol. 293, No. 3, 1074-1083).*
Lin (Medicinal Chemistry Research (2015), 24(7), 2898-2905).*
IPRP2 in PCTEP2016070118, Aug. 11, 2017.
Li-Gen Lin et al., Naturally Occurring Homoisoflavonoids and Their Pharmacological Activities, Planta Medica, 2014, pp. 1053-1066; XP055249523, vol. 80, No. 13.
Santos-Zea et al., Agave (*Agave* spp.) adn its Traditional Products as a Source of Bioactive Compounds, Current Bioactive Compounds, 2012, pp. 1-14, vol. 8, No. 3.
Search Report and Written Opinion in EP15183639, dated Feb. 2, 2016.
Search Report and Written Opinion in PCTEP2016070118, dated Nov. 10, 2016.
B. Stephen Inbarah, et al.; Simultaneous determination of phenolic acides and flavonoids in Lycium barbarum Linnaeus by HPLC_DAD-EI-MS; Journal of Pharmaceutical and Biomedical Analysis,; 2010; pp. 549-556; 51.
Kim LE, et al.; Identification and quantification of antioxidants in Fructus Lycii; Food Chemistry; 2007; pp. 353-363; 105.
Zhang et al.,; Homoisoflavonoids from Polygonatum odoratum; Journal of Natural Productcs; 2010; pp. 548-552; vol. 73, No. 4.
Maya Mikulic-Petkovsek; HPLC_MSn identification and quantification of flavonol glycosides in 28 wild and cultiavted berry species,; Food Chemistry; 2012; pp. 2138-2146; 135.

(Continued)

*Primary Examiner* — Shaojia A Jiang
*Assistant Examiner* — Michael C Henry
(74) *Attorney, Agent, or Firm* — Foley & Lardner LLP

(57) ABSTRACT

Foods or meals high in available carbohydrate such as sucrose or starch increase postprandial blood glucose concentrations. According to Node et al. (Cardiovascular diabetology, 8, 23 (2009)), repeated high post-prandial plasma glucose "spikes" are associated with an increased risk of developing type II diabetes. Unregulated glycemic excursions are undesirable, and any reduction or "blunting" of the post-prandial glucose concentration in blood is potentially beneficial. This invention relates to an edible composition for delay of intestinal glucose uptake through synergistic inhibition of both active sodium glucose co-transporter 1 (SGLT1) and passive glucose transporter 2 (GLUT2) leading to flattening or blunting of the post-prandial glucose peak. Thus in a first aspect of the invention, an edible composition provided in the form of a single serving of one or more unit dosages comprising a combination of 2 to 200 mg of at least one homoisoflavonoid and 20 to 2000 mg of at least one flavonoid monoglucoside, and salts thereof.

19 Claims, 1 Drawing Sheet

(56) References Cited

OTHER PUBLICATIONS

Nguyen Thi Hoang Anh, et al.; Phytochemical study on the plants of the antidrug medication heantos 4; Vietnam Jouranl of Chemistry; 2013; pp. 358-363; 51(3).
Jian-Ya Qian, et al.; The Efficienty of flavonoids in po0lar extracts of lycium chinense Mill fruits as free readical scavenger; Food Chemistry,; 2004; pp. 283-288; 87.
C.C. Wang, ; Isolation of carotenoids, flavonoids and polysaccharides from *Lycium barbarum* L. and evaluation of antioxidant activity; Food Chemistry; 2010; pp. 184-192; 120.
Herbal Hot Water Mix for Diabetes; Mintel GNPD ; 2013; pp. 1-2, Record ID 2235325.
Saundarya Ashoka Tonic for Ladies; Mintel GNPD; 2014; pp. 1-2, reocrd ID 2825101.
Full Veggie Enzyme Drink; Mintel GNPD; 2014; pp. 1-2, Record ID 2053969.
Supplement Tablets for Diabetes; Mintel GNPD; 2011; pp. 1-2, Record ID 1550661.
Blueberry Compote with Agave Syrup; Mintel GNPD.; pp. 1-2, Record ID 2359578.

* cited by examiner

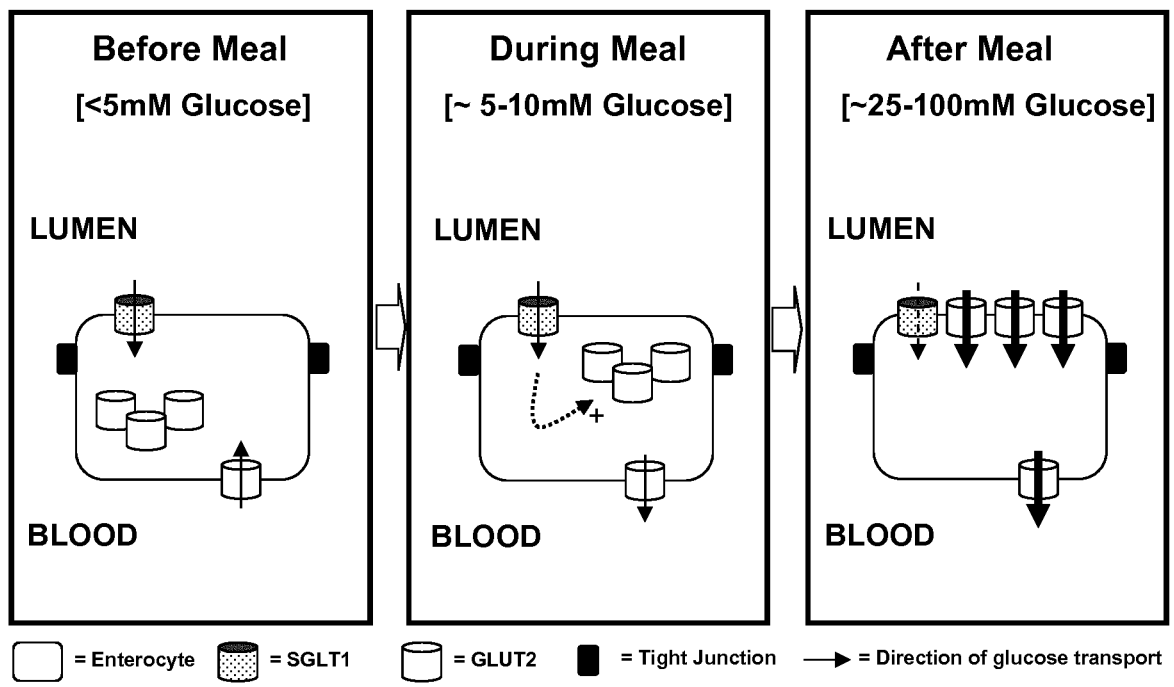

EDIBLE COMPOSITION

Foods or meals high in available carbohydrate such as sucrose or starch increase postprandial blood glucose concentrations. According to Node et al. (Cardiovascular diabetology, 8, 23 (2009)), repeated high post-prandial plasma glucose "spikes" are associated with an increased risk of developing type II diabetes. Unregulated glycemic excursions are undesirable, and any reduction or "blunting" of the post-prandial glucose concentration in blood is potentially beneficial. This invention relates to an edible composition for delay of intestinal glucose uptake through synergistic inhibition of both active sodium glucose co-transporter 1 (SGLT1) and passive glucose transporter 2 (GLUT2) leading to flattening or blunting of the post-prandial glucose peak.

WO 2012/168108 (Unilever et al) discloses an edible composition for delay of intestinal glucose uptake through synergistic inhibition of both active sodium glucose co-transporter 1 (SGLT1) and passive glucose transporter 2 (GLUT2) leading to flattening or blunting of the post-prandial glucose peak. In particular an edible composition is provided comprising at least 5 percent dry weight at least one flavonoid aglycone and at least 5 percent dry weight at least one flavonoid glucoside, wherein the flavonoid glucoside is at least 20 percent, preferably at least 40 percent, most preferably at least 60 percent more resistant to hydrolysis by lactase phloridzin hydrolase than quercetin-4-glucoside, and wherein the flavonoid aglycone is a GLUT 2 inhibitor and the flavonoid glucoside is a SGLT 1 inhibitor.

WO 2014/086632 (Unilever et al) discloses an edible composition for delay of intestinal glucose uptake through synergistic inhibition of both active sodium glucose co-transporter 1 (SGLT1) and passive glucose transporter 2 (GLUT2) leading to flattening or blunting of the post-prandial glucose peak. In particular an edible composition is provided in the form of a single serving of one or more unit dosages wherein the edible composition comprises 20-2000, preferably 30-1000, most preferably 40-500 mg a 3,5-dihydroxy-trans-stilbene and 10-2000, preferably 20-1000, most preferably 40-500 mg flavonoid monoglucoside or dihydrochalcone monoglucoside.

Zhang et al (J. Nat. Prod., 73, 548-552 (2010)) reports that the ethyl acetate soluble fraction of a 90% methanol extract of the fibrous roots of *Polygonatum odoratum* was found to potentiate insulin-stimulated glucose uptake in differentiated 3T3-L1 adipocytes. Bioassay-guided fractionation yielded nine homoisoflavonoids, together with an isoflavone glycoside and a flavanone glycoside. The homoisoflavonoids include 5,7-dihydroxy-3-(4'-hydroxybenzyl)-6-methyl-8-methoxychroman-4-one (EA2) and 5,7-di hydroxy-3-(4'-hydroxybenzyl)-6,8-dimethylchroman-4-one (EA3), and the isoflavone glycoside is tectoridin. The results indicate that homoisoflavonoids may be potential insulin sensitizers.

SUMMARY OF THE INVENTION

In a glucose transport cell model based on Caco-2 cells (heterogeneous human epithelial colorectal adenocarcinoma cells), it was observed that there was a statistically significant synergistic down regulation in glucose transport across the cells following treatment with a selective mixtures of homoisoflavonoids (GLUT2 inhibitors) and flavonoid monoglucosides (SGLT1 inhibitors) compared to treatment with either compound alone, or their notional additive performance.

Thus in a first aspect of the invention, an edible composition provided in the form of a single serving of one or more unit dosages is provided, the edible composition comprising a combination of 2 to 200 mg of at least one homoisoflavonoid and 20 to 2000 mg of at least one flavonoid monoglucoside, and salts thereof. These levels of the at least one homoisoflavonoid and the at least one flavonoid monoglucoside and salts thereof are such as to produce a synergistic reduction in post-prandial blood glucose peak amplitude or glycemic response.

According to Lin et al (Planta Med, 80, 1053-1066 (2014)), homoisoflavonoids are a subclass of flavonoids rarely found in Nature. They can be found mainly in the Fabacae and Asparagacae families. They can be divided in the sub-classes: sappanin-type; scillascillin-type; brazilin-type; caesalpin-type; and protosappanin-type.

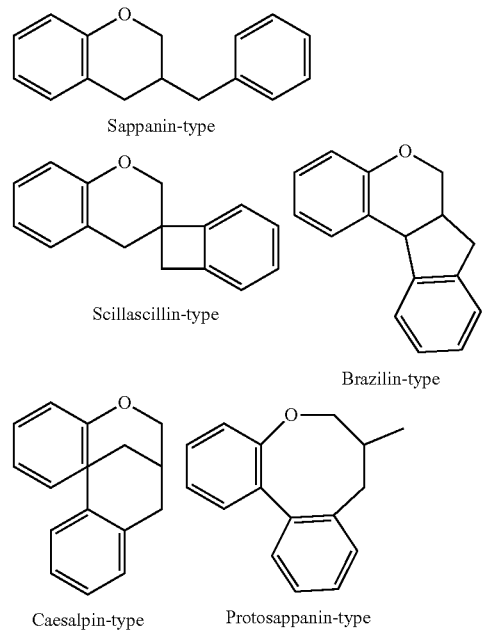

In a second aspect of the invention, a method of reducing post-prandial blood glucose peak amplitude or glycemic response in a non-diabetic person is provided, the method comprising the steps of:
 (a) oral administration of the edible composition of the first aspect of the invention to the non-diabetic person; and
 (b) oral administration of saccharide to the non-diabetic person;
wherein step (a) is simultaneous with, precedes by 0 to 90, preferably 0 to 60 minutes, or follows by 0 to 30 minutes step (b), and
wherein the saccharide comprises or is glucose.

In a third aspect of the invention, a method for treatment of a person with type 2 diabetes is provided, the method comprising the steps of:
 (a) oral administration of the edible composition of the first aspect of the invention to the person in need thereof; and
 (b) oral administration of saccharide to the person in need thereof;
wherein step (a) is simultaneous with, precedes by 0 to 90, preferably 0 to 60 minutes, or follows by 0 to 30 minutes step (b), and wherein the saccharide comprises or is glucose.

In a fourth aspect of the invention, the edible composition according to the first aspect of the invention is provided for use in reducing post-prandial blood glucose peak amplitude or glycemic response in a non-diabetic person.

In a fifth aspect of the invention, the edible composition of the first aspect of the invention is provided for use in the treatment of type 2 diabetes.

In a sixth aspect of the invention, use of the edible composition of the first aspect of the invention is provided for the manufacture of a medicament for reducing post-prandial blood glucose peak amplitude or glycemic response in a non-diabetic person.

In a seventh aspect of the invention, use of the edible composition of the first aspect of the invention is provided for the manufacture of a medicament for treatment of type 2 diabetes.

BRIEF DESCRIPTION OF THE FIGURES

The invention is illustrated with reference to:
FIG. 1 which shows a model of the glucose concentration timeline during a meal.

DETAILED DESCRIPTION OF THE INVENTION

In a first aspect of the invention, an edible composition provided in the form of a single serving of one or more unit dosages is provided, the edible composition comprising a combination of 2 to 200 mg of at least one homoisoflavonoid and 20 to 2000 mg of at least one flavonoid monoglucoside, and salts thereof. These levels of the at least one homoisoflavonoid and the at least one flavonoid monoglucoside and salts thereof are such as to produce a synergistic reduction in post-prandial blood glucose peak amplitude or glycemic response.

Preferably the edible composition comprises at least 5 mg, more preferably at least 10 mg, more preferably still at least 15 mg, and preferably at most 100 mg, more preferably at most 50 mg, more preferably still at most 25 mg of the at least one homoisoflavonoid, Preferably the edible composition comprises at least 50 mg, more preferably at least 100 mg, more preferably still at least 150 mg, and preferably at most 1000 mg, more preferably at most 500 mg, more preferably still at most 250 mg of the at least one flavonoid monoglucoside, Preferably the at least one homoisoflavonoid is a sappanin-type homoisoflavonoid. Preferably the sappanin-type homoisoflavonoid is a 3-benzylchroman-4-one type homoisoflavonoid. Preferably the homoisoflavonoid has structure I:

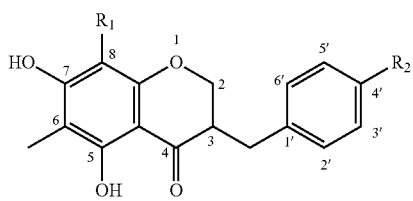

wherein $R_1$ is —H or -Me; and
wherein $R_2$ is —OH, —OMe or —O—$CH_2$—O—($C_{3'}$).
Preferably the homoisoflavonoid is selected from the group consisting of 5,7-dihydroxy-3-(4'-hydroxybenzyl)-6-methylchroman-4-one (EA1), 5,7-di hydroxy-3-(4'-hydroxybenzyl)-6-methyl-8-methoxychroman-4-one (EA2), 5,7-dihydroxy-3-(4'-hydroxybenzyl)-6,8-dimethylchroman-4-one (EA3), methylophiopogonanone A (MOA) and methylophiopogonanone B (MOB).

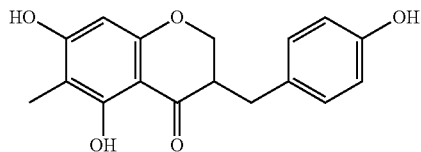 [SMILES: Cc1c(O)cc2c(c1O)C(=O)C(Cc1ccc(O)cc1)CO2]

5,7-dihydroxy-3-(4'-hydroxybenzyl)-6-methylchroman-4-one (EA1)

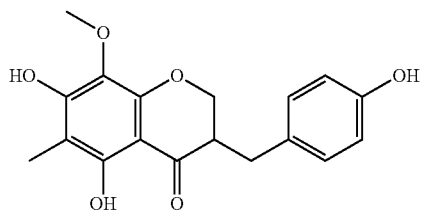 [SMILES: COc1c(O)c(C)c(O)c2c1OCC(Cc1ccc(O)cc1)C2=O]

5,7-dihydroxy-3-(4'-hydroxybenzyl)-6-methyl-8-methoxychroman-4-one (EA2)

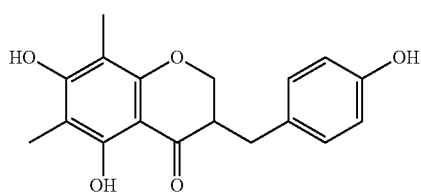 [SMILES: Cc1c(O)c(C)c2c(c1O)C(=O)C(Cc1ccc(O)cc1)CO2]

5,7-dihydroxy-3-(4'-hydroxybenzyl)-6,8-dimethylchroman-4-one (EA3)

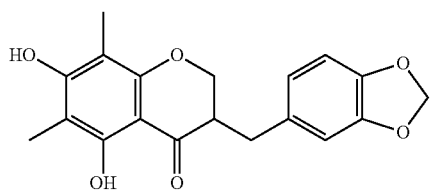 [SMILES: Cc1c(O)c(C)c2c(c1O)C(=O)C(Cc1ccc3c(c1)OCO3)CO2]

methylophiopogonanone A (MOA)

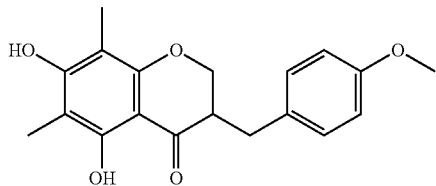 [SMILES: COc1ccc(CC2COc3c(C)c(O)c(C)c(O)c3C2=O)cc1]

methylophiopogonanone B (MOB)

Preferably the at least one flavonoid monoglucoside and salts thereof are selected from the group consisting of a flavone monoglucoside, a flavonol monoglucoside, a flavanone monoglucoside, an isoflavone monoglucoside and an anthocyanin, and salts thereof. Preferably the at least one flavonoid monoglucoside and salts thereof are selected from the group consisting of luteolin-7-glucoside, tectoridin, delphinidin-3-O-glucoside chloride (myrtillin chloride), kaempferol-3-glucoside, naringenin-7-O-glucoside and apigenin-8-C-glucoside.

Preferably the molar ratio of flavonoid monoglucoside and salts thereof to homoisoflavonoid is at least 1, preferably at least 5, most preferably at least 10.

In a second aspect of the invention, a method of reducing post-prandial blood glucose peak amplitude or glycemic response in a non-diabetic person is provided, the method comprising the steps of:
(a) oral administration of the edible composition of the first aspect of the invention to the non-diabetic person; and
(b) oral administration of saccharide to the non-diabetic person;
wherein step (a) is simultaneous with, precedes by 0 to 90, preferably 0 to 60 minutes, or follows by 0 to 30 minutes step (b), and
wherein the saccharide comprises or is glucose.

Preferably the saccharide may be selected from the group consisting of polysaccharide, oligosaccharide, disaccharide, monosaccharide and mixtures thereof.

In a third aspect of the invention, a method for treatment of a person with type 2 diabetes is provided, the method comprising the steps of:
(a) oral administration of the edible composition of the first aspect of the invention to the person in need thereof; and
(b) oral administration of saccharide to the person in need thereof;
wherein step (a) is simultaneous with, precedes by 0 to 90, preferably 0 to 60 minutes, or follows by 0 to 30 minutes step (b), and
wherein the saccharide comprises or is glucose.

In a fourth aspect of the invention, the edible composition according to the first aspect of the invention is provided for use in reducing post-prandial blood glucose peak amplitude or glycemic response in a non-diabetic person.

In a fifth aspect of the invention, the edible composition of the first aspect of the invention is provided for use in the treatment of type 2 diabetes.

In a sixth aspect of the invention, use of the edible composition of the first aspect of the invention is provided for the manufacture of a medicament for reducing post-prandial blood glucose peak amplitude or glycemic response in a non-diabetic person.

In a seventh aspect of the invention, use of the edible composition of the first aspect of the invention is provided for the manufacture of a medicament for treatment of type 2 diabetes.

Example 1: Identification of SGLT1 and GLUT2 Inhibitors

Method
Routine Cell Culture

Human epithelial colorectal adenocarcinoma (Caco-2) cells were obtained from the American Type Culture Collection (ATCC) and cultured in Growth Medium consisting of Dulbecco's modified Eagle's medium (containing Glutamax-1, 4.5 g/L D-glucose and 25 mM 4-(2-hydroxyethyl)-1-piperazine ethanesulphonic acid (Hepes) (Invitrogen)), 10% foetal bovine serum (Sigma), 1% non-essential amino acids (Invitrogen) and 1 mM sodium pyruvate (Sigma)). The cells were routinely passaged at approximately 80% confluence using TrypLE™ Express Stable Trypsin-Like Enzyme (Invitrogen) to detach the cells, and seeded at approximately 114 cells per $mm^2$ in fresh tissue culture flasks. Only cells between the passage numbers 45 and 49 were used for experiments.

Preparation of Differentiated Caco-2 Cell Monolayers

Corning® HTS Transwell® 96 well permeable insert supports (Sigma) were collagen coated with 40 μl of 50 μg/ml rat tail collagen type I (BD Biosciences) in 0.02 M acetic acid for one hour at room temperature under sterile conditions. The inserts were washed twice in phosphate buffered saline (PBS (Invitrogen)) and the Caco-2 cells seeded into the inserts at $1.0 \times 10^6$ cell/ml (75 μl per insert) in Growth Medium and 30 ml of Growth Medium added to the feeder plate below. The cells were left to attach to the collagen matrix and form monolayers over 48 hours at 37° C., 5% $CO_2$. Both inserts and feeder plate were washed in PBS and the cells incubated with BD Entero-STIM™ Enterocyte Differentiation Medium containing MITO+™ Serum Extender solution (both BD Biosciences), 75 μl per insert and 30 ml in the feeder plate, for a further 48 hours at 37° C., 5% $CO_2$.

Glucose Transport Inhibitor Cell Screening Assay

Differentiated cell monolayers were washed gently in Dulbecco's Phosphate Buffered Saline containing $CaCl_2$ and $MgCl_2$ (PBS(+) (Invitrogen)) and the inserts transferred to a new Corning® HTS Transwell®-96 well receiver plate (Sigma). The cells were incubated with fresh PBS(+) (75 μl per insert and 225 μl per well) for 60 minutes at 37° C., 5% $CO_2$. The PBS(+) was gently aspirated and replaced with 75 μl per insert of either 5 mM D-glucose (Sigma)±test compound or 25 mM D-glucose±test compound in triplicate and 225 μl per well of PBS(+) quickly added to each well. The 5 mM glucose wells and the 25 mM glucose wells were incubated at 37° C., 5% $CO_2$ for 15 minutes and 30 minutes, respectively. Details of all the compounds tested are found in Table 1. The cell inserts were transferred to a new receiver plate, the supernatant gently aspirated from the cells and replaced with 100 μl of 100 μM of Lucifer Yellow (Sigma) solution to confirm the integrity of the monolayers. 225 μl of PBS(+) was added to each well and incubated at 37° C., 5% $CO_2$ for 1 hour. The cell inserts were then discarded and the permeability of the membranes to Lucifer Yellow checked by measuring the fluorescence of the samples at 485 nm (excitation) and 530 nm (emission) on a Spectramax Gemini EM fluorescence microplate reader.

Glucose Assay

The amount of glucose transported across the cell monolayers was measured using a glucose assay based on Invitrogen's Amplex Red Glucose/Glucose oxidase Assay Kit. Briefly, 50 µl of each test sample was transferred to a black sided/clear bottom 96-well plate (Greiner Bio-One) to which 100 µl of reaction buffer (0.5 µl 10 mM Ampliflu Red, 1 µl 10 U/ml Horse Radish peroxidase, 1 µl 100 U/ml glucose oxidase and 97.5 µl PBS (all Sigma)) was added. After 10 minutes incubation at room temperature, the fluorescence of the samples was measured at 530 nm (excitation) and 590 nm (emission) on a Spectramax Gemini EM fluorescence microplate reader and the glucose concentration extrapolated from a standard curve.

Results

Table 1 shows the percentage of inhibition of each test compound against the transport of glucose across a differentiated Caco-2 cell monolayer. At the lower D-glucose concentration of 5 mM, the early transport of glucose across the cell monolayer is predominantly through the apically expressed, high affinity, low capacity SGLT1 glucose transporter. At higher D-glucose concentrations, the SGLT1 transporter becomes saturated and consequently the majority of glucose transport across the monolayer is driven by the low affinity, high capacity GLUT2 transporter that is targeted to the apical membrane only following an initial SGLT1-dependent transport of glucose. The screening cell model, detailed in the methods above, is designed to take advantage of these differences in the optimal conditions for each transporter to identify both SGLT1 and GLUT2 specific inhibitors. While both SGLT1 and GLUT2 on the apical membrane transport glucose into the enterocyte, GLUT2 is also expressed in the basolateral membrane where it is essential for the transport of glucose out of the cell. Hence, GLUT2 specific inhibitors will not only block the apically targeted transporters at high D-glucose concentrations (25 mM), they will also enter the cell and block the exit of glucose from the enterocyte at low D-glucose concentrations (5 mM). Therefore, to differentiate between inhibition of apical and basolateral transporters, each compound was tested at both 5 mM D-glucose for 15 minutes and 25 mM D-glucose for 30 minutes. Compounds were classed as SGLT1 inhibitors if they exhibited at least 20% inhibition of glucose transport at 5 mM D-glucose and a corresponding no more than 20% inhibition at 25 mM D-glucose. Compounds that were able to inhibit glucose transport by at least 20% in both conditions were classed as GLUT2 specific inhibitors. This approach was qualified through the use of the widely recognised specific inhibitors of both SGLT1 and GLUT2, namely phloridzin and phloretin respectively.

The foregoing glucose transport cell model was described by Kellett et al. (Diabetes, 54, 10, 3056-62 (2005)) and, with reference to FIG. 1, is designed to mimic the localised changes in glucose concentration in the small intestine during the consumption of a carbohydrate rich meal. Before the meal, the concentration of free glucose in the lumen of the intestine is low (<5 mM) and the apically expressed SGLT1 transporter actively transports any available glucose into the enterocyte. GLUT2 transporters are also active on the basolateral membrane of the enterocyte, transporting glucose from the blood into the cell to maintain cellular metabolism if required. During a meal, the local concentration of glucose begins to increase (5-10 mM) and is transported from the intestinal lumen by SGLT1 and subsequently into the systemic circulation via GLUT2. As a consequence of this initial glucose transport across the enterocyte, intracellular stores of GLUT2 are mobilised and targeted to the apical membrane. Shortly after the meal, very high local concentrations of glucose occur (25-100 mM) as the carbohydrate content of the meal is broken down into monosaccharides by alpha-glucosidase enzymes located on the apical enterocyte membrane. At these high levels of glucose, the high affinity, low capacity transporter SGLT1 becomes saturated and the majority of glucose transport across the enterocyte is due to the low affinity, high capacity GLUT2 transporters now present in the apical membrane.

Table 1 demonstrates that for inhibition of SGLT1, a flavonoid monoglucoside or dihydrochalcone monoglucoside is required as confirmed by phloridzin, tectoridin and delphinidin-3-O-glucoside chloride (myrtillin chloride).

Table 1 of WO 2014/086632 (Unilever et al) discloses further examples of SGLT1 inhibitors, all being flavonoid monoglucosides, such as luteolin-7-glucoside, apigenin-7-glucoside, apigenin-8-c-glucoside, kaempferol-3-glucoside, kaempferol-7-glucoside, quercetin-3-glucoside, quercetin-4-glucoside, naringenin-7-glucoside, eriodictiol-7-glucoside, daidzein-8-C-glucoside, daidzein-7-glucoside, cyanidin-3-glucoside, malvidin-3-O-glucoside, delphinidin-3-glucoside and pelargonidin-3-glucoside. Indeed, the presence of an additional glucose moiety on the chemical structure destroys this inhibitory action as demonstrated by quercetin-3,4'-diglucoside. The specificity for a glucoside is confirmed by the absence of SGLT1 inhibitory activity by other flavonoid glycosides tested, including cyanidin-3-rutinoside and malvidin-3-O-galactoside. In addition, the lack of SGLT1 inhibitory activity shown by the hydroquinone monoglucoside, arbutin, reinforces the importance of a flavonoid and dihydrochalcone structures in the glucoside molecule.

Table 1 also shows that all five homoisolflavonoids, EA1, EA2, EA3, MOA and MOB are GLUT2 inhibitors.

TABLE 1

Compounds tested for SGLT1 and GLUT2 inhibition activity in Caco-2 cells using 5 mM D-glucose for 15 minutes and 25 mM D-glucose for 30 minutes, respectively. The assigned class of transporter inhibited by each compound is based on SGLT1 inhibitors having ≥20% inhibition of glucose transport at 5 mM D-glucose and ≤20% inhibition at 25 mM D-glucose, and GLUT2 inhibitors having ≥20% inhibition at both 5 mM and 25 mM D-glucose levels. Triplicate values for % glucose transport inhibition.

| Chemical family | Test compound* | Solvent | % Glucose transport inhibiton | | Class[#] | Supplier |
| --- | --- | --- | --- | --- | --- | --- |
| | | | 5 mM | 25 mM | | |
| Isoflavones | Tectoridin | DMSO | 29.41 ± 0.62 | 4.92 ± 2.08 | SGLT1 | SIGMA |
| Anthocyanin | Delphinidin-3-O-glucoside chloride (myrtillin chloride) | DMSO | 41.00 ± 3.60 | 12.82 ± 1.19 | SGLT1 | Extrasynthase |

TABLE 1-continued

Compounds tested for SGLT1 and GLUT2 inhibition activity in Caco-2 cells using
5 mM D-glucose for 15 minutes and 25 mM D-glucose for 30 minutes, respectively. The
assigned class of transporter inhibited by each compound is based on SGLT1 inhibitors
having ≥20% inhibition of glucose transport at 5 mM D-glucose and ≤20% inhibition at
25 mM D-glucose, and GLUT2 inhibitors having ≥20% inhibition at both 5 mM and 25 mM
D-glucose levels. Triplicate values for % glucose transport inhibition.

| Chemical family | Test compound* | Solvent | % Glucose transport inhibiton 5 mM | 25 mM | Class[#] | Supplier |
|---|---|---|---|---|---|---|
| Chalcone | Phloridzin | DMSO | 37.00 ± 3.76 | 14.27 ± 0.84 | SGLT1 | SIGMA |
| Homoisoflavonoid | EA1 | DMSO | 90.68 ± 1.40 | 66.57 ± 5.21 | GLUT2 | Extracted from *Polygonatum odoratum* |
| Homoisoflavonoid | EA2 | DMSO | 89.90 ± 0.06 | 62.96 ± 2.94 | GLUT2 | Extracted from *Polygonatum odoratum* |
| Homoisoflavonoid | EA3 | DMSO | 91.15 ± 0.46 | 67.40 ± 5.87 | GLUT2 | Extracted from *Polygonatum odoratum* |
| Homoisoflavonoid | MOA | DMSO | 39.33 ± 2.17 | 27.73 ± 3.70 | GLUT2 | Shanghai PureOne, Biotechnology Co. Ltd. |
| Homoisoflavonoid | MOB | DMSO | 46.24 ± 2.04 | 30.61 ± 3.20 | GLUT2 | Shanghai PureOne, Biotechnology Co. Ltd. |

*All compounds tested at 300 μM; phloridzin is a positive control for SGLT1 inhibitors.
[#]Based on SGLT1 inhibitors having >20% inhibition at 5 mM glucose and <20% inhibition at 25 mM glucose, and GLUT2 inhibitors having >20% inhibition at both 5 mM and 25 mM glucose.

Conclusion

Tectoridin and delphinidin-3-O-glucoside chloride (myrtillin chloride) were identified using the Caco-2 cell assay as inhibitors of SGLT1. The homoisolflavonoids, EA1, EA2, EA3, MOA and MOB were identified using the Caco-2 cell assay as inhibitors of GLUT2.

Example 2: Extraction and Isolation of Compounds from *Polygonatum odoratum* (Fragrant Solomonseal)

Method

Dried root part of *Polygonatum odoratum* (Fragrant Solomonseal) (1.0 kg) was extracted with an aqueous solution of 95% ethanol for 2 hours at a solid-liquid weight ratio of 1:4. The remaining plant root was then extracted with an aqueous solution of 70% ethanol for 2 hours at a solid-liquid weight ratio of 1:3. The two aqueous ethanol extracts were then combined, concentrated, and vacuum dried, to yield 333.1 g (yield rate 33.3%) *Polygonatum odoratum* aqueous ethanol extract.

The dried extract was dissolved in water and partitioned in sequence with petroleum ether, ethyl acetate, and 1-butanol to obtain 21.0 g petroleum ether extract (yield rate 6.3%), 4.33 g ethyl acetate extract (yield rate 1.3%), 29.3 g 1-butanol extract (yield rate 8.8%) and 216.5 g water extract (yield rate 65.0%).

The ethyl acetate extract was further purified using an LC3000 semi-preparative HPLC system fitted with an YMC-Pack-C18 column (250 mm×10 mm, 5 μm) eluted with an isocratic solvent system containing about 60% acetonitrile and about 40% water with 0.18% formic acid, monitored at 280 nm, at a flow rate of 6 ml/minute providing 38.3 mg 5,7-dihydroxy-3-(4'-hydroxybenzyl)-6-methylchroman-4-one (EA1) (yield rate 0.885%), 59.0 mg 5,7-dihydroxy-3-(4'-hydroxybenzyl)-6-methyl-8-methoxychroman-4-one (EA2) (yield rate 1.362%), 93.8 mg 5,7-dihydroxy-3-(4'-hydroxybenzyl)-6,8-dimethylchroman-4-one (EA3) (yield rate 2.167%).

Conclusion

An ethyl acetate extract of an aqueous ethanol extract of a dried root part of *Polygonatum odoratum* was found to comprise 5,7-dihydroxy-3-(4'-hydroxybenzyl)-6-methylchroman-4-one (EA1), 5,7-dihydroxy-3-(4'-hydroxybenzyl)-6-methyl-8-methoxychroman-4-one (EA2), 5,7-dihydroxy-3-(4'-hydroxybenzyl)-6,8-dimethylchroman-4-one (EA3). Tectoridin was not identified as an extraction product.

Example 3: Synergy Between SGLT1 Inhibitors and Homoisoflavonoids Materials 5,7-Dihydroxy-3-(4'-hydroxybenzyl)-6-methylchroman-4-one (EA1) (from Example 2)
5,7-Dihydroxy-3-(4'-hydroxybenzyl)-6-methyl-8-methoxychroman-4-one (EA2) (from Example 2)
5,7-Dihydroxy-3-(4'-hydroxybenzyl)-6,8-dimethylchroman-4-one (EA3) (from Example 2)
Methylophiopogonanone A (MOA) (Shanghai PureOne, Biotechnology Co. Ltd.)
Methylophiopogonanone B (MOB) (Shanghai PureOne, Biotechnology Co. Ltd.)
Method
Preparation of Differentiated Caco-2 Cell Monolayers
Caco-2 cells were cultured and routinely passaged as described in Example 1. Caco-2 cells were seeded into BioCoat HTS Fibrillar Collagen Multiwell Inserts (BD Biosciences) at 2.5×10⁵ cell/ml (500 μl per insert) in Growth Medium and 30 ml of Growth Medium added to the feeder plate below. The cells were left to attach to the collagen matrix and form monolayers over 24 hours at 37° C., 5% $CO_2$. Both inserts and feeder plate were washed in PBS and the cells incubated with BD Entero-STIM™ Enterocyte Differentiation Medium containing MITO+™ Serum Extender solution (both BD Biosciences), 500 µl per insert and 30 ml in feeder plate, for a further 48 hours at 37° C., 5% $CO_2$.

Glucose Transport Cell Model

Differentiated cell monolayers were washed gently in PBS(+) and the inserts transferred to a new standard tissue culture 24-well plate. The cells were incubated with fresh PBS(+) (500 µl per insert and 1 ml per well) for 30 minutes at 37° C. 5% $CO_2$. The PBS(+) was gently aspirated and replaced with 250 µl per insert of 5 mM D-glucose±test compound and 1 ml of PBS(+) quickly added to each well below before the cells were replaced in the incubator at 37° C. 5% $CO_2$. After 15 minutes, the cell inserts were transferred to a new 24-well plate, and a further 250 µl of 45 mM D-glucose±test compound was added to each insert (resulting in a final concentration of glucose of 25 mM) and again 1 ml of PBS(+) added to the wells. After a further 15 minutes the inserts were again transferred to a new 24-well plate and this time only fresh PBS(+) was added to the wells below. This step was repeated after another 15 minutes. The cell inserts were transferred to a new 24-well plate, the supernatant gently aspirated from the cells and replaced with 500 µl of 100 µM of Lucifer Yellow (Sigma) solution to confirm the integrity of the monolayers. 1 ml of PBS(+) was added to each well and incubated at 37° C., 5% $CO_2$ for 1 hour. The cell inserts were then discarded and the permeability of the membranes to Lucifer Yellow was checked by measuring the fluorescence of the samples at 485 nm (excitation) and 530 nm (emission) on a Spectramax Gemini EM fluorescence microplate reader.

Glucose Assay

After the last incubation, all of the retained PBS(+) from each step (i.e. at 15, 30, 45 and 60 minutes) was assayed for glucose levels as described in Example 1, and the total cumulative glucose transport calculated. The localised changes in luminal glucose concentrations described and illustrated in example 1 are mimicked in-vitro through an initial short incubation of differentiated Caco-2 cells with a low level of D-glucose (5 mM for 15 minutes) immediately followed by a sustained incubation with a high level of D-glucose (final concentration of 25 mM for 45 minutes).

Results

Table 2 summarises the results using the above-mentioned Caco-2 assay with combinations of selected homisoflavonoids and SGLT1 inhibitors (a variety of flavonoid monoglucosides) and clearly show that in combination, both SGLT1 inhibitors and homoisoflavonoids can synergistically inhibit the localised uptake of glucose from the intestinal lumen and hence reduce the high 'spikes' of postprandial blood glucose associated with the onset of type 2 diabetes.

TABLE 2

Cumulative glucose transport and standard deviation (duplicate) for combination of known SGLT1 inhibitors and selected homoisoflavonoids. 5,7-dihydroxy-3-(4'-hydroxybenzyl)-6-methylchroman-4-one (EA1); 5,7-dihydroxy-3-(4'-hydroxybenzyl)-6-methyl-8-methoxychroman-4-one (EA2); 5,7-dihydroxy-3-(4'-hydroxybenzyl)-6,8-dimethylchroman-4-one (EA3); methylophiopogonanone A (MOA); methylophiopogonanone B (MOB).

| Synergy | Synergy | 5 mM | 25 mM | Cumulative (AVE) glucose transport | Cumulative (SD) glucose transport |
|---|---|---|---|---|---|
| Isoflavone monoglucoside & homoisoflavonoid | Tectoridin (T, 300 uM) & EA1 (10 uM) | NC | NC | 430.33 | 12.16 |
| | | NC | T | 395.85 | 24.48 |
| | | NC | EA1 | 301.50 | 11.90 |
| | | T | NC | 346.92 | 15.09 |
| | | T | EA1 | 231.73 | 6.40 |
| Isoflavone monoglucoside & homoisoflavonoid | Tectoridin (T, 300 uM) & EA-1 (5 uM) | NC | NC | 343.7 | 8.96 |
| | | NC | T | 304.5 | 13.75 |
| | | NC | EA-1 | 284.6 | 9.55 |
| | | T | NC | 321.4 | 11.02 |
| | | T | EA-1 | 257.8 | 7.99 |
| Flavone monoglucoside & homoisoflavonoid | Luteolin-7-glucoside (L7G, 300 uM) & EA1 (10 uM) | NC | NC | 309.42 | 16.57 |
| | | NC | L7G | 256.73 | 13.76 |
| | | NC | EA1 | 232.03 | 10.44 |
| | | L7G | NC | 220.63 | 5.73 |
| | | L7G | EA1 | 149.05 | 5.66 |
| Flavone monoglucoside & homoisoflavonoid | Luteolin-7-glucoside (L7G, 300 uM) & EA-1 (2.5 uM) | NC | NC | 365.0 | 6.71 |
| | | NC | L7G | 281.9 | 8.72 |
| | | NC | EA-1 | 339.2 | 11.91 |
| | | L7G | NC | 301.4 | 10.39 |
| | | L7G | EA-1 | 260.7 | 14.53 |
| Anthocyanin & homoisoflavonoid | Myrtillin chloride (MC, 300 uM) & MOB (5 uM) | NC | NC | 257.15 | 13.00 |
| | | NC | MC | 227.60 | 11.38 |
| | | NC | MOB | 200.59 | 18.33 |
| | | MC | NC | 220.62 | 9.05 |
| | | MC | MOB | 141.10 | 7.54 |
| Flavanone monoglucoside & homoisoflavonoid | Naringenin-7-O-glucoside (N7G, 300 uM) & MOB (5 uM) | NC | NC | 257.15 | 13.00 |
| | | NC | N7G | 236.65 | 8.24 |
| | | NC | MOB | 200.59 | 18.33 |
| | | N7G | NC | 215.32 | 7.67 |
| | | N7G | MOB | 144.25 | 8.24 |
| Flavonol monoglucoside & homoisoflavonoid | Kaempferol-3-glucoside (K3G, 150 uM) & EA2 (10 uM) | NC | NC | 385.96 | 9.44 |
| | | NC | K3G | 290.49 | 10.04 |
| | | NC | EA2 | 283.98 | 13.36 |
| | | K3G | NC | 297.72 | 9.35 |
| | | K3G | EA2 | 182.41 | 12.11 |

TABLE 2-continued

Cumulative glucose transport and standard deviation (duplicate) for combination of
known SGLT1 inhibitors and selected homoisoflavonoids. 5,7-dihydroxy-3-(4'-hydroxybenzyl)-
6-methylchroman-4-one (EA1); 5,7-dihydroxy-3-(4'-hydroxybenzyl)-6-methyl-8-methoxychroman-
4-one (EA2); 5,7-dihydroxy-3-(4'-hydroxybenzyl)-6,8-dimethylchroman-4-one (EA3);
methylophiopogonanone A (MOA); methylophiopogonanone B (MOB).

| Synergy | Synergy | 5 mM | 25 mM | Cumulative (AVE) glucose transport | Cumulative (SD) glucose transport |
|---|---|---|---|---|---|
| Isoflavone monoglucoside & homoisoflavonoid | Tectoridin (T, 300 uM) & MOA (5 uM) | NC | NC | 327.43 | 5.73 |
|  |  | NC | T | 298.98 | 16.55 |
|  |  | NC | MOA | 231.69 | 17.90 |
|  |  | T | NC | 298.40 | 2.65 |
|  |  | T | MOA | 186.11 | 2.62 |
| Flavone monoglucoside & homoisoflavonoid | Apigenin-8-C-glucoside (A8G, 300 uM) & EA3 (2.5 uM) | NC | NC | 304.99 | 4.00 |
|  |  | NC | A8G | 287.58 | 11.08 |
|  |  | NC | EA3 | 291.33 | 16.24 |
|  |  | A8G | NC | 291.89 | 12.53 |
|  |  | A8G | EA3 | 237.69 | 5.14 |

In the above table, every test pairing of a homisoflavonoid (HIF) and a flavonoid monoglucoside (FM) has 5 values reported:

1. No Compound (NC)+NC
2. NC+HIF (data not used for synergy calculation
3. NC+HIF
4. FM+NC
5. FM+HIF Pair 1 provides the baseline.
Pair 3 shows inhibition due to HIF alone.
Pair 4 shows inhibition due to FM alone.
Pair 5 shows inhibition due to combination of HIF and FM.

Synergy is achieved when the inhibition caused by the combination of HIF and FM is greater than the sum of the inhibition due to HIF alone added to the inhibition due to FM alone.

It will be noted that for the pairing of Tectoridin (T, 300 uM) & EA1 (10 uM) a synergistic effect was not observed. This was due to the saturation of inhibition by the high level of EA1 (10 uM). This pairing was therefore repeated with a lower level of EA1 (5 uM) and hence, without the saturation of inhibition by EA1, the synergistic effect was observed.

Similarly, it will be noted that for the pairing of Luteolin-7-glucoside (L7G, 300 uM) & EA1 (10 uM) a synergistic effect was not observed. This was, again, due to the saturation of inhibition by the high level of EA1 (10 uM). This pairing was therefore repeated with a lower level of EA1 (2.5 uM) and hence, without the saturation of inhibition by EA1, the synergistic effect was observed.

Conclusions

SGLT1 inhibitors and homoisoflavonoids synergistically inhibit the localised uptake of glucose from the intestinal lumen and hence reduce the high 'spikes' of postprandial blood glucose associated with the onset of type 2 diabetes.

The SGLT1 inhibitors were flavonoid monoglucosides based on five sub-classes of flavonoid, namely an isoflavone, two flavones, an anthocyanidin, a flavanone, and a flavonol. The selected homoisoflavonoids were 5,7-dihydroxy-3-(4'-hydroxybenzyl)-6-methylchroman-4-one (EA1); 5,7-dihydroxy-3-(4'-hydroxybenzyl)-6-methyl-8-methoxychroman-4-one (EA2); 5,7-dihydroxy-3-(4'-hydroxybenzyl)-6,8-dimethylchroman-4-one (EA3); methylophiopogonanone A (MOA); methylophiopogonanone B (MOB).

The invention claimed is:

1. An edible composition provided in the form of a single serving of one or more unit dosages comprising:
   2 to 200 mg of at least one homoisoflavonoid; and
   20 to 2000 mg of at least one flavonoid monoglucoside, and salts thereof,
   wherein:
   the at least one homoisoflavonoid is selected from the group consisting of 5,7-dihydroxy-3-(4'-hydroxybenzyl)-6-methylchroman-4-one (EA1), 5,7-dihydroxy-3-(4'-hydroxybenzyl)-6,8-dimethylchroman-4-one (EA3), methylophiopogonanone A (MOA) and methylophiopogonanone B (MOB); and
   the molar ratio of the at least one flavonoid monoglucoside, and salts thereof to the at least one homoisoflavonoid is at least about 60:1.

2. An edible composition according to claim 1 wherein the at least one flavonoid monoglucoside and salts thereof are selected from the group consisting of a flavone monoglucoside, a flavonol monoglucoside, a flavanone monoglucoside, an isoflavone monoglucoside and an anthocyanin, and salts thereof.

3. An edible composition according to claim 1 wherein the at least one flavonoid monoglucoside and salts thereof are selected from the group consisting of luteolin-7-glucoside, tectoridin, delphinidin-3-O-glucoside chloride (myrtillin chloride), kaempferol-3-glucoside, naringenin-7-O-glucoside and apigenin-8-C-glucoside.

4. An edible composition according to claim 1 for use in reducing post-prandial blood glucose peak amplitude or glycemic response in a non-diabetic person.

5. An edible composition according to claim 1 for use in the treatment of type 2 diabetes.

6. An edible composition according to claim 1 wherein the composition comprises 5 to 100 mg of at least one homoisoflavonoid and 50 to 1000 mg of at least one flavonoid monoglucoside, and salts thereof.

7. An edible composition according to claim 6 wherein the composition comprises 15 to 25 mg of at least one homoisoflavonoid and 100 to 250 mg of at least one flavonoid monoglucoside, and salts thereof.

8. An edible composition according to claim 1 wherein the composition comprises a concentration of 2.5 to 10 µM of at least one homoisoflavonoid and 150 to 300 µM of at least one flavonoid monoglucoside, and salts thereof.

9. An edible composition according to claim 7 wherein the at least one flavonoid monoglucoside and salts thereof are selected from the group consisting of luteolin-7-glucoside, tectoridin, delphinidin-3-O-glucoside chloride (myrtillin chloride), kaempferol-3-glucoside, naringenin-7-O-glucoside and apigenin-8-C-glucoside.

10. An edible composition according to claim 8 wherein the at least one flavonoid monoglucoside and salts thereof are selected from the group consisting of luteolin-7-glucoside, tectoridin, delphinidin-3-O-glucoside chloride (myrtillin chloride), kaempferol-3-glucoside, naringenin-7-O-glucoside and apigenin-8-C-glucoside.

11. An edible composition provided in the form of a single serving of one or more unit dosages comprising:
    2 to 200 mg of at least one homoisoflavonoid; and
    20 to 2000 mg of at least one flavonoid monoglucoside, and salts thereof,
    wherein:
        the at least one homoisoflavonoid is 5,7-dihydroxy-3-(4'-hydroxybenzyl)-6-methyl-8-methoxychroman-4-one (EA2); and
        the molar ratio of the at least one flavonoid monoglucoside, and salts thereof to the at least one homoisoflavonoid is at least 10:1.

12. An edible composition according to claim 11 wherein the at least one flavonoid monoglucoside and salts thereof are selected from the group consisting of luteolin-7-glucoside, tectoridin, delphinidin-3-O-glucoside chloride (myrtillin chloride), kaempferol-3-glucoside, naringenin-7-O-glucoside and apigenin-8-C-glucoside.

13. An edible composition according to claim 11 wherein the composition comprises 5 to 100 mg of at least one homoisoflavonoid and 50 to 1000 mg of at least one flavonoid monoglucoside, and salts thereof.

14. An edible composition according to claim 11 wherein the composition comprises a concentration of 2.5 to 10 μM of at least one homoisoflavonoid and 150 to 300 μM of at least one flavonoid monoglucoside, and salts thereof.

15. A method of reducing post-prandial blood glucose peak amplitude or glycemic response in a non-diabetic person comprising the steps of:
    a. oral administration of the edible composition of claim 11 to the non-diabetic person; and
    b. oral administration of saccharide to the non-diabetic person;
        wherein step (a) is simultaneous with, precedes by 0 to 90, or follows by 0 to 30 minutes step (b), and
        wherein the saccharide comprises or is glucose.

16. A method for treatment of a person with type 2 diabetes comprising the steps of:
    c. oral administration of the edible composition of claim 11 to the person in need thereof; and
    d. oral administration of saccharide to the person in need thereof;
        wherein step (a) is simultaneous with, precedes by 0 to 90, or follows by 0 to 30 minutes step (b), and
        wherein the saccharide comprises or is glucose.

17. A method of reducing post-prandial blood glucose peak amplitude or glycemic response in a non-diabetic person comprising the steps of:
    a. oral administration of the edible composition of claim 1 to the non-diabetic person; and
    b. oral administration of saccharide to the non-diabetic person;
        wherein step (a) is simultaneous with, precedes by 0 to 90, or follows by 0 to 30 minutes step (b), and
        wherein the saccharide comprises or is glucose.

18. A method for treatment of a person with type 2 diabetes comprising the steps of:
    c. oral administration of the edible composition of claim 1 to the person in need thereof; and
    d. oral administration of saccharide to the person in need thereof;
        wherein step (a) is simultaneous with, precedes by 0 to 90, or follows by 0 to 30 minutes step (b), and
        wherein the saccharide comprises or is glucose.

19. A The method according to claim 18, wherein the saccharide may be selected from the group consisting of polysaccharide, oligosaccharide, disaccharide, monosaccharide and mixtures thereof.

* * * * *